(12) United States Patent
Guziak et al.

(10) Patent No.: US 8,240,217 B2
(45) Date of Patent: Aug. 14, 2012

(54) DIAPHRAGM ISOLATION FORMING THROUGH SUBTRACTIVE ETCHING

(75) Inventors: Robert Guziak, Thousand Oaks, CA (US); Enrique Gandaria, Valencia, CA (US)

(73) Assignee: Kavlico Corporation, Moorpark, CA (US)

( * ) Notice: Subject to any disclaimer, the term of this patent is extended or adjusted under 35 U.S.C. 154(b) by 1176 days.

(21) Appl. No.: 11/872,596

(22) Filed: Oct. 15, 2007

(65) Prior Publication Data

US 2009/0098318 A1 Apr. 16, 2009

(51) Int. Cl.
*G01L 7/08* (2006.01)

(52) U.S. Cl. .......................... 73/715; 73/716; 361/283.4

(58) Field of Classification Search .................. None
See application file for complete search history.

(56) References Cited

U.S. PATENT DOCUMENTS

| | | | |
|---|---|---|---|
| 3,988,153 A | 10/1976 | Politycki | |
| 4,543,266 A | 9/1985 | Matsuo | |
| 4,581,250 A | 4/1986 | Armstrong | |
| 4,754,243 A | 6/1988 | Armstrong | |
| 5,096,791 A | 3/1992 | Yahalom | |
| 5,589,810 A * | 12/1996 | Fung | 338/4 |
| 5,654,244 A * | 8/1997 | Sakai et al. | 438/53 |
| 5,672,551 A * | 9/1997 | Fung | 438/53 |
| 5,888,845 A | 3/1999 | Bashir | |
| 6,229,190 B1 * | 5/2001 | Bryzek et al. | 257/419 |
| 6,441,451 B1 * | 8/2002 | Ikeda et al. | 257/418 |
| 6,503,823 B1 * | 1/2003 | Ravesi | 438/622 |
| 6,584,852 B2 * | 7/2003 | Suzuki et al. | 73/718 |
| 6,756,248 B2 * | 6/2004 | Ikeda et al. | 438/53 |
| 6,802,222 B2 * | 10/2004 | Ishio et al. | 73/718 |
| 6,877,383 B2 * | 4/2005 | Horie et al. | 73/754 |
| 7,029,829 B2 | 4/2006 | Stark | |
| 7,040,173 B2 * | 5/2006 | Dehe | 73/706 |
| 7,066,031 B2 * | 6/2006 | Zdeblick et al. | 73/715 |
| 7,125,786 B2 * | 10/2006 | Ring et al. | 438/571 |
| 7,179,668 B2 * | 2/2007 | Baney et al. | 438/22 |
| 7,499,604 B1 * | 3/2009 | Burns | 385/12 |
| 2007/0163355 A1 | 7/2007 | Nassar | |

FOREIGN PATENT DOCUMENTS

| | | |
|---|---|---|
| JP | 57171899 | 10/1982 |
| JP | 62294196 | 12/1987 |
| JP | 2001036994 | 2/2001 |
| JP | 2006150340 | 6/2006 |

OTHER PUBLICATIONS

D. M. Rowe et al., IECEC-98-024—33d Intersociety Energy Conversion Engineering Conference, Colorado Springs, CO, Aug. 2-6, 1998.

(Continued)

*Primary Examiner* — Lisa Caputo
*Assistant Examiner* — Jermaine Jenkins
(74) *Attorney, Agent, or Firm* — Gilman Clark & Hunter LLC

(57) ABSTRACT

Described herein is a housing comprising an inside and at least one sidewall, wherein the at least one sidewall comprises inner and outer surfaces. An etch stop deposit is disposed over at least a portion of the housing, and a diaphragm material deposit is disposed over at least a portion of the etch stop deposit.

22 Claims, 7 Drawing Sheets

OTHER PUBLICATIONS

Hill, Lisa R., et al., Shape Memory Alloy Film for Deployment and Control of Membrane Apertures; UV/Optical/IR Space Telescopes: Innovative Technologies and Concepts, San Diego, CA, Aug. 3-5, 2003, Bellingham, WA, Society of Photo-Optical Instrumentation Engineers (SPIE Proceedings, vol. 5166) p. 271-280.

Heinen, D. et al., On the Mechanical Strength of Free-Standing and Substrate-Bonded Aluminum Thin Films, J. Appl. Phys., vol. 77, No. 8, Apr. 14, 1995.

Rosenmayer, C. T., et al., Preparation of Free-Standing CVD Tungsten Thin Films for Mechanical Testing, Measurement Science and Technology, vol. 2, No. 1, Jan. 1991.

Mineta, T., et al., Shape Memory Thin Film for Blood Vessel Holding Actuator of Thrombus Detector, Key Engineering Materials (Switzerland) pt. 1, vol. 297-300, 2005.

Salvadori, M. C., et al., Fabrication of Free-Standing Diamond Membranes, Thin Solid Films, vol. 290-291, Dec. 15, 1996.

\* cited by examiner

DIAPHRAGM ISOLATION FORMING THROUGH SUBTRACTIVE ETCHING

FIELD OF THE INVENTION

The present invention relates generally to housing construction, and more particularly, to housings having diaphragms deposited thereon and methods to produce diaphragms.

BACKGROUND OF THE INVENTION

Diaphragms and membranes are structures that play a critical role in pressure and temperature sensors. Diaphragms are usually used in pressure sensors such that the pressure is usually measured by detecting and quantifying the deflection of a diaphragm onto which pressure is applied. Diaphragms also help isolate two different media and still allow transmission of pressure from one medium to another. This is normally done to protect a pressure-sensing element from an incompatible environment by encapsulating the sensor in a housing that is filled with a neutral fluid such as silicone oil. The external pressure is transmitted to the oil, and therefore to the pressure sensor, through the membrane. The membrane also functions to "isolate" one environment from the other. Typically, the diaphragms and isolation membranes are attached to the housing by methods such as welding, brazing, machined in, or stamped and adhesively bonded. Typically, these attachment methods cause the final structure stress. In addition, these attachment methods are difficult to implement when the application requires very small diaphragms or membranes (i.e., diaphragms and membranes having very small diameters, or sizes). An example of such applications is implantable medical catheters used to measure pressure inside the body.

SUMMARY TO THE PREFERRED EMBODIMENTS

In accordance with one aspect of the present invention, there is provided a housing having an inside and inner and outer surfaces. An etch stop deposit is disposed over at least a portion of the outer surface. A diaphragm material deposit is disposed over at least a portion of the etch stop deposit.

In accordance with another aspect of the present invention, there is provided a method of isolating a diaphragm on a housing. The method comprises the steps of depositing an etch stop deposit on at least a portion of an outside of the housing, depositing a diaphragm material deposit on at least a portion of the etch stop material, and etching at least a portion of an inside of the housing, thereby exposing at least a portion of the etch stop deposit to an inside of the housing.

In accordance with another aspect of the present invention, there is provided a housing that includes an inside and inner and outer surfaces. The outer surface includes a diaphragm forming surface. An etch stop deposit is disposed over at least a portion of the diaphragm forming surface. A diaphragm material deposit is disposed over at least a portion of the etch stop deposit. Preferably, at least a portion of the inner surface is etchable, thereby exposing the etch stop deposit to the inside.

In accordance with another aspect of the present invention, there is provided a conduit comprising an inside and inner and outer surfaces. An etch stop deposit is disposed over at least a portion of the outer surface. A diaphragm material deposit is disposed over at least a portion of the etch stop deposit.

In accordance with another aspect of the present invention, there is provided a plate comprising front and back surfaces. A diaphragm material deposit is disposed over at least a portion of the front surface. A mask is disposed over at least a portion of the back surface. At least a portion of the back surface is etchable, thereby exposing the diaphragm material deposit.

In accordance with another aspect of the present invention, there is provided a housing having an inside, at least one end, and at least one sidewall, wherein each of the end and the sidewall comprises inner and outer surfaces. An etch stop deposit is disposed over at least a portion of the outer surface. A diaphragm material deposit is disposed over at least a portion of the etch stop deposit. Preferably, the housing includes a protective deposit disposed over at least a portion of the diaphragm material deposit. Preferably, at least a portion of the housing is removable, thereby exposing at least a portion of the etch stop deposit to the inside. In a preferred embodiment, at least a portion of the end and/or the sidewall is removable, thereby exposing the etch stop deposit to the inside. Preferably, at least a portion of the housing is removed by etching.

In accordance with another aspect of the present invention, there is provided a housing having an inside, at least one end, and at least one sidewall, wherein each of the end and the sidewall comprises inner and outer surfaces. The housing includes an etch stop deposit disposed over at least a portion of the housing and a diaphragm material deposit disposed over at least a portion of the etch stop deposit. Preferably, at least a portion of the housing is removable, thereby exposing the etch stop deposit to the inside. Preferably, at least a portion of the housing is removable, thereby exposing the etch stop deposit to the outside.

In accordance with another aspect of the present invention, there is provided a method of isolating a diaphragm on a housing. The method comprises depositing an etch stop deposit on at least a portion of the housing and depositing a diaphragm material deposit on at least a portion of the etch stop deposit. Preferably, the method comprises etching at least a portion of an inside of the housing, thereby exposing at least a portion of the etch stop deposit to an inside of the housing. In another aspect of the present invention, the method comprises etching at least a portion of an outside of the housing, thereby exposing at least a portion of the etch stop deposit to the exterior of the housing.

In accordance with another aspect of the present invention, there is provided a plate comprising front and back surfaces. A plurality of diaphragm structures are disposed over at least a portion of the front surface. At least a portion of the back surface of the plate is etchable, thereby exposing the plurality of diaphragm structures. Preferably, at least one diaphragm structure is cut apart from the plate.

In accordance with another aspect of the present invention, there is provided a housing comprising an inside and at least one sidewall, wherein the at least one sidewall comprises inner and outer surfaces. The housing comprises an etch stop deposit disposed over at least a portion of the housing and a diaphragm material deposit disposed over at least a portion of the etch stop deposit. Preferably, at least a portion of the housing has been removed, thereby exposing the etch stop deposit to the inside. In another aspect of the present invention, at least a portion of the housing has been removed, thereby exposing the etch stop deposit to the exterior. Preferably, the housing further comprises at least one end, wherein at least a portion of the at least one end has been removed. Preferably, the etch stop deposit may be selected from the group consisting of gold, platinum, or rhodium.

In accordance with another aspect of the present invention, there is provided a plate comprising a front and back surfaces and an etch stop deposit disposed on at least a portion of the front surface, and a diaphragm material deposit disposed over at least a portion of the etch stop deposit, wherein at least a portion of the back surface is etched, thereby exposing the diaphragm material deposit. Preferably, the plate further comprises a mask disposed over at least a portion of the back surface. The plate may comprise a protective deposit disposed over at least a portion of the diaphragm material deposit.

In accordance with another aspect of the present invention, there is provided a structure. The structure comprises front and back surfaces, a plurality of etch stop deposits disposed over at least a portion of the front surface, and a plurality of diaphragm material deposits each disposed over at least a portion of one of the etch stop deposits, wherein portions of the back surface is etched, thereby exposing at least a portion of each of the plurality of etch stop deposits. In one aspect of this embodiment, the invention comprises a method of forming a plurality of plates. The method comprises the steps of (a) providing the foregoing structure and cutting the structure to provide a plurality of plates.

BRIEF DESCRIPTION OF THE DRAWINGS

The invention may be more readily understood by referring to the accompanying drawings in which.

Like numerals refer to like parts throughout the several views of the drawings.

DETAILED DESCRIPTION OF THE PREFERRED EMBODIMENTS

The present invention is directed to housings, preferably sensor housings, and methods of forming diaphragms on the housings. The diaphragm is generally used to separate materials, such as corrosive materials, from the sensitive sense element in the pressure sensor. Preferably, the methods of forming diaphragms on the housings include subtractive etching. The diaphragm is formed on the housing itself. As such, methods such as stamping and welding, machining, stamping and adhesively bonding, brazing, or positively forming the diaphragm over a sacrificial element is not needed. The diaphragm formation requires no copper slugs, mandrels, or the like. A functional diaphragm forming is not utilized. Preferably, the housing itself is the electroforming template as well as the final end product. These methods are particularly suited for producing miniature diaphragms and isolation membranes that cannot be easily attached to the rest of the mechanical system. In addition, the inventive methods of the invention allow for forming a diaphragm with minimal stress concentration and reduction of or elimination of cracking, leading to longer life under dynamic stress loading and corrosion effects.

In a preferred embodiment, the housing is a sensor housing, preferably, a pressure sensor. The pressure sensor measures pressure, typically of gases and fluids. The pressure sensor is used in applications where high numbers of pressure and temperature cycles are required. The sensor is intended to be used primarily in medical applications implanted in the body. Generally, the physical size of the sensor is 7 french or 4 french (50-85 thousands of an inch in diameter) and 0.1 to 0.3 inches typically in length, or applied in flat plate capsules requiring special processing for handling. However, the housings/diaphragms of the present invention may also be used in force transducers, temperature sensors, and/or combination pressure/temperature sensors and/or any other implantable device, without departing from the scope of the present invention.

In a preferred embodiment, the method of forming diaphragms on a housing may be described as follows: A housing is coated with an etch stop deposit; the etch stop deposit is coated with a diaphragm material deposit; and the diaphragm material deposit is coated with a protective deposit. Subsequently, at least a portion of the housing is removed, thereby exposing the etch stop deposit to the inside of the housing.

Figure 11:
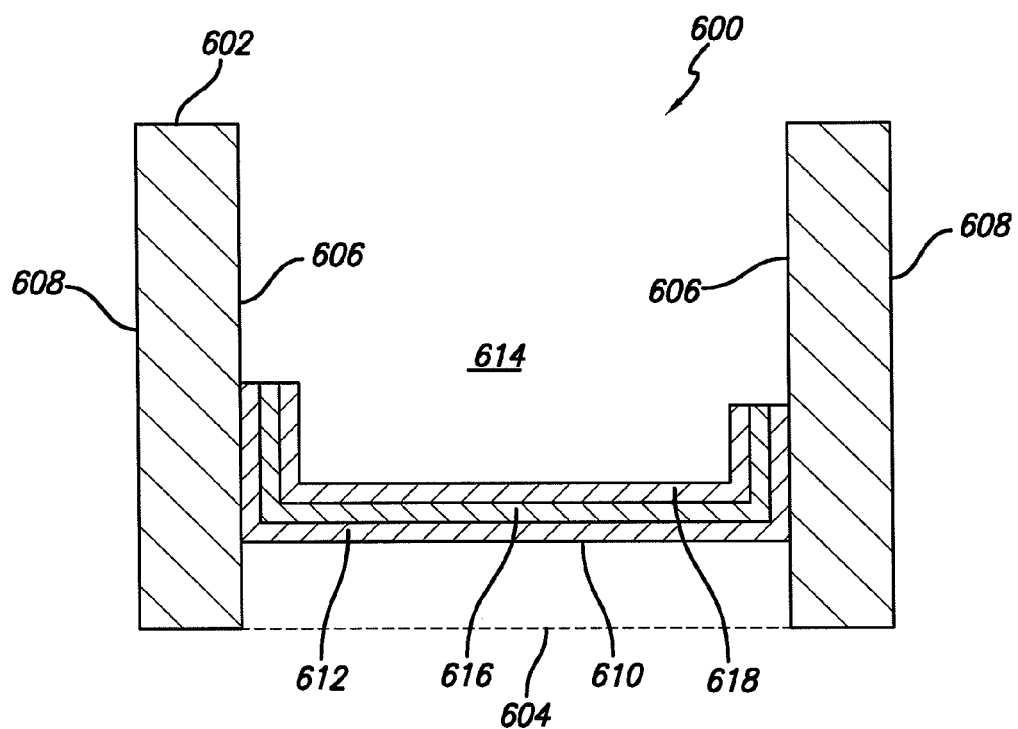
FIG. 11 is a cross-sectional view of a housing on which a diaphragm is formed on an inner surface near an end of the housing of FIG. 1, in accordance with another preferred embodiment of the invention.
Figure 12:
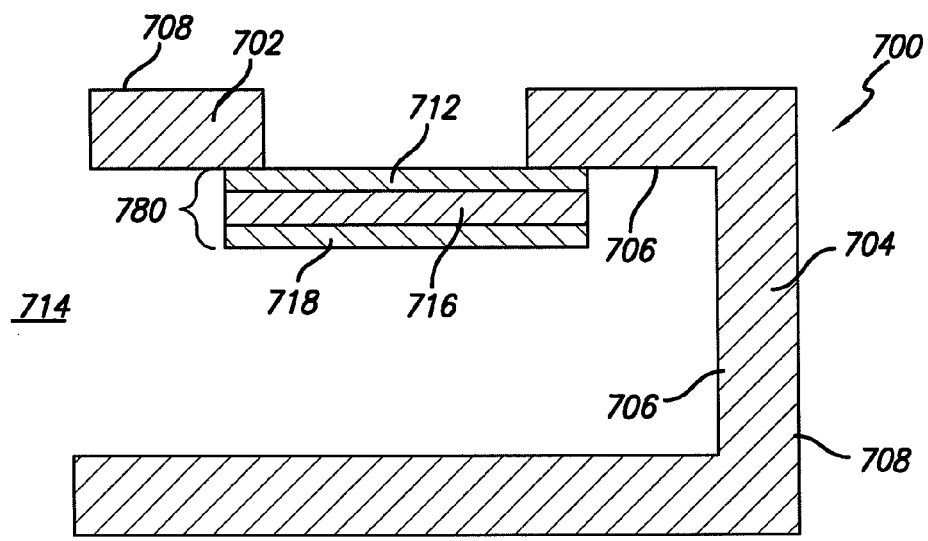
FIG. 12 is a cross-sectional view of a housing on which a diaphragm is formed on an inner surface of a sidewall in accordance with another preferred embodiment of the present invention.

As will be discussed in detail below, FIGS. 1-5, FIG. 7, and FIG. 11 refer to a housing on which a diaphragm will be formed or has been formed on an end or front of a tubular or rectangular housing. For example, a housing on which a diaphragm is formed on the end may be used in a cylinder for a catheter, or may be used in a pacemaker lead. FIG. 6 and FIG. 12 refer to a housing on which a diaphragm has been formed on a sidewall of a tubular or rectangular housing. Generally, a housing that is tubular in shape has one sidewall, and a housing that is rectangular in shape has four sidewalls. In addition, FIGS. 1-10 refer to housings and methods of forming housings on which a diaphragm structure has been formed on the outside of the housing, and are thereby etched from the inside. FIGS. 11-12 refer to housings having diaphragm structures formed on the inside, and are thereby etched from the outside.

It is to be understood that FIGS. 1-5 and FIG. 10 and the discussion with respect to these figures, pertain to both tubular and rectangular housings, diaphragms formed from ends and sidewalls of the housings, as well as diaphragms formed on the inside and outside of the housings. Preferably, the housing is a conduit. However, the housing may be of any shape and size without departing from the scope of the present invention. For example, the housing may have a variety of different cross-section sizes.

Figure 1:
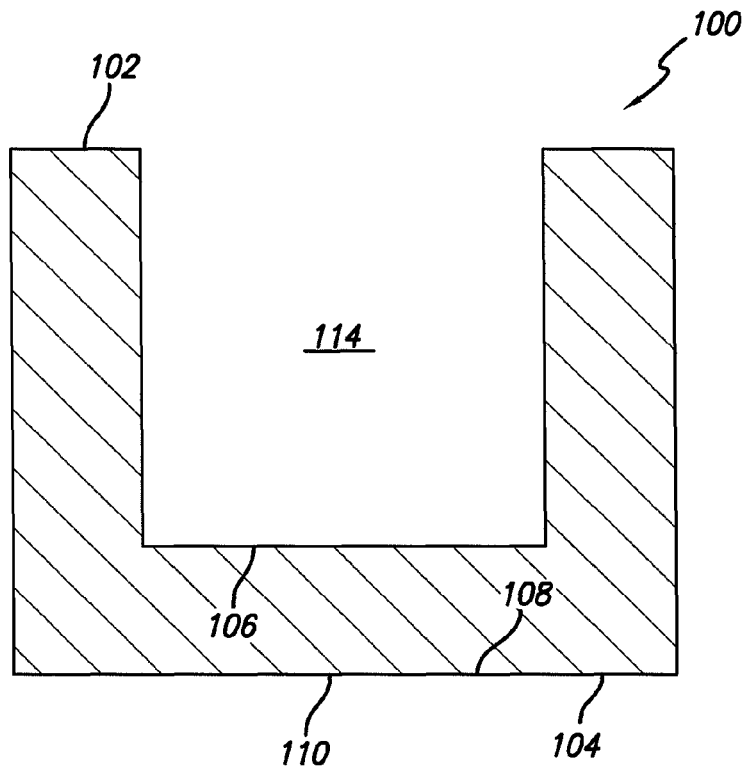
FIG. 1 is a cross-sectional view of a housing on which a diaphragm will be formed in accordance with a preferred embodiment of the present invention.

FIG. 1 shows a housing 100 on which a diaphragm will be formed on an end. In a preferred embodiment, the housing 100 includes at least one sidewall 102 and at least one end 104 surrounding an inside or interior 114. Each of the sidewall 102 and the end 104 includes inner surface 106 and outer surface 108. The outer surface 108 preferably includes a diaphragm-forming surface 110. The diaphragm-forming surface 110 preferably is the outermost layer of the outer surface 108. The diaphragm-forming surface 110 is preferably cleaned prior to diaphragm forming.

In a preferred embodiment, housing 100 is comprised of metal. Examples of metals used in the construction of the housing include stainless steel, titanium, platinum, platinum iridium, MP35 titanium, and stainless steel such as 316 or 304. Plastics or ceramics which may have metals electroplated to the surface may also be used. However, the housing 100 may be formed of a variety of materials as is known to one skilled in the art.

In a preferred embodiment, the sidewall 102 and/or the end 104 of the housing 100 is manufactured to be thicker prior to being removed, or etched. As such, the interior 114 of the housing 100 generally defines a smaller volume prior to removal, or etching.

In a preferred embodiment, the outer surface 108 of the end 104, such as the diaphragm-forming surface 110, is substantially flat. As such, the diaphragm formed thereon may be substantially flat. However, the outer surface 108 of the end 104 may not be substantially flat; the outer surface 108 of the end 104 may include a plurality of ridges on a corrugated surface or other protrusions and/or indentations. For example, the outer surface 108 of the end 104 may have a dimpled surface pattern, bumped surface pattern and/or any other pattern. In addition, the diaphragm may be round (such as for use on a catheter tip), rectangular (such as for applications that use a side-mounted diaphragm), or oval (to eliminate stress concentration), or crescent-shaped. Therefore, the finished diaphragm may be shaped in a variety of patterns, as it will preferably take on the shape of the outer surface 108 of the end 104.

Figure 2:
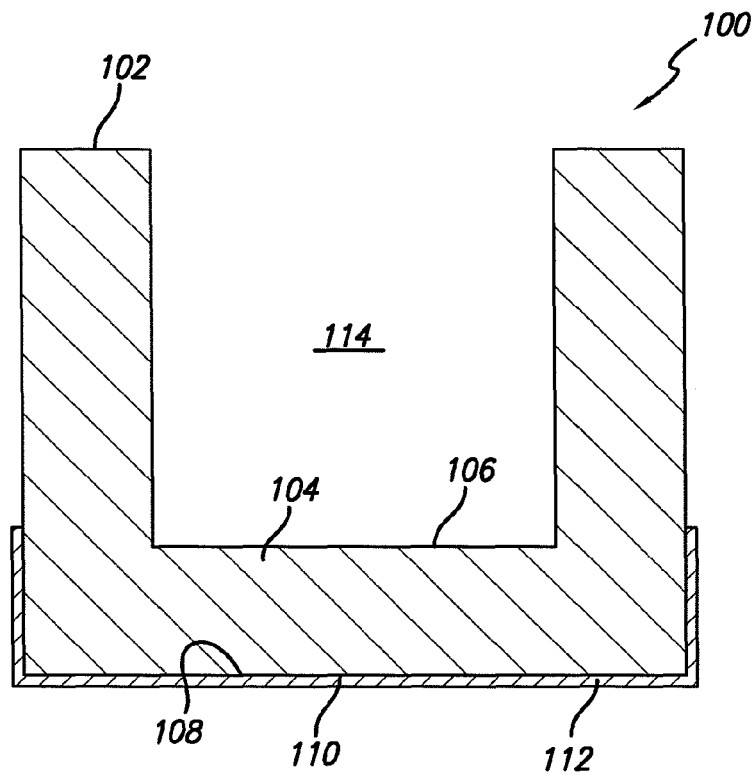
FIG. 2 is a cross-sectional view of the housing of FIG. 1 with an etch stop deposit disposed thereon.

FIG. 2 shows a preferred embodiment of the housing 100 of FIG. 1 after an etch stop deposit or layer 112 has been disposed on a portion of the outer surface 108 of the end 104. Preferably, the etch stop deposit 112 is comprised of gold and is not removable through etching. For example, etch stop deposit 112 may be made of gold, platinum, rhodium, or the like.

However, the etch stop deposit may be any other material that is not fully removable or only partially removable, either through etching or any other means that is known in the art, such as other chemical or thermal means, that serve to remove one substrate and not another.

In a preferred embodiment, the etch stop deposit 112 is electroplated onto the housing 100. However, the etch stop deposit 112 may be deposited onto the housing using sputtering or any other deposition technique known in the art, without departing from the scope of the present invention. In addition, instead of an etch stop layer, a mask may be used.

Figure 3:
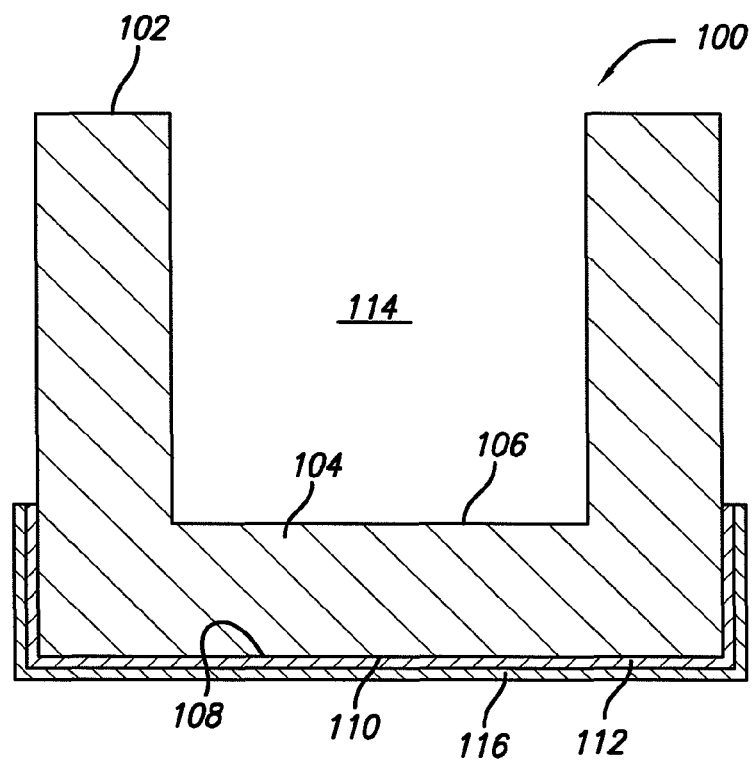
FIG. 3 is a cross-sectional view of the housing of FIG. 1 with a diaphragm deposit material disposed on the etch stop deposit.

FIG. 3 shows a preferred embodiment of the housing 100 after a diaphragm material deposit 116 has been disposed on at least a portion of the etch stop layer 112. Diaphragm material deposit 116 may also be disposed on at least a portion of the outer surface 108 of the housing 100. Preferably, the diaphragm material deposit 116 is comprised of nickel, nickel-cobalt, and/or chromium. However, the diaphragm material deposit 116 may be comprised of any other suitable material, as is known in the art, without departing from the scope of the present invention.

In a preferred embodiment, electroplating and/or electrodeposition, such as a simple wide tolerance electrodeposition and/or nickel cobalt zero stress electroforming, is used to deposit diaphragm material deposit 116 over at least a portion of the etch stop deposit 112. However, sputtering and/or any other technique known in the art may be used to deposit the diaphragm material 116 onto the etch stop deposit 112 and/or housing 100.

Diaphragm material deposit 116 is typically formed to a specific layer thickness, depending on the application and/or the need. Preferably, diaphragm material deposit 116 is thicker than etch stop deposit 112. However, diaphragm material deposit 116 may be of the same or less thickness than the etch stop deposit 112.

Figure 4:
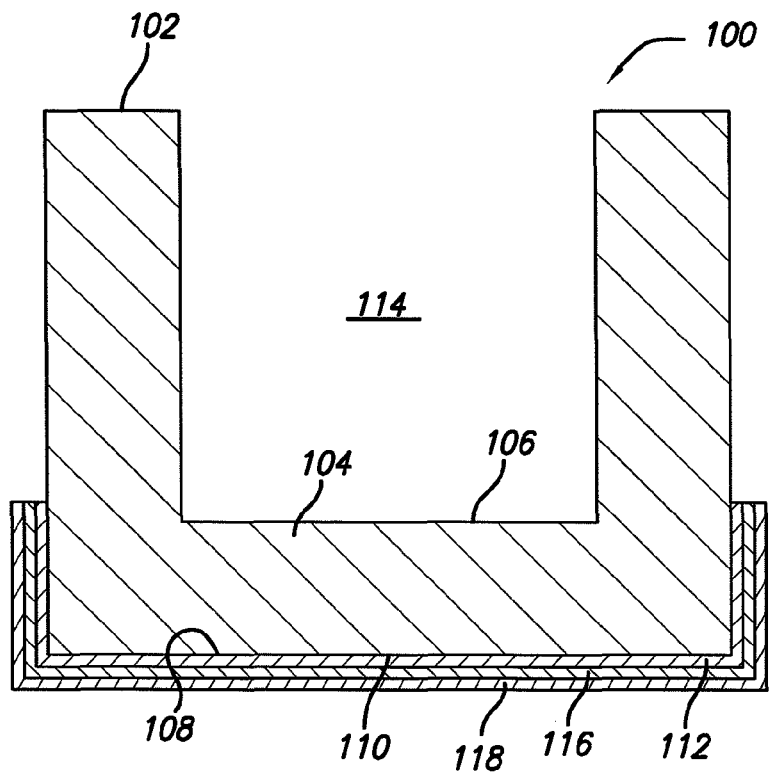
FIG. 4 is a cross-sectional view of the housing of FIG. 1 with a protective deposit disposed on the diaphragm material deposit.

FIG. 4 shows a preferred embodiment of the housing 100 after a protective deposit 118 has been disposed on at least a portion of the diaphragm material deposit 116. Protective deposit 118 may also be disposed over at least a portion of the housing 100 and/or the etch stop deposit 112. However, the protective deposit layer 118 may be omitted, without departing from the scope of the present invention.

Preferably, the protective deposit 118 is comprised of gold. However, the protective deposit 118 may be comprised of any other material, as is known in the art, without departing from the scope of the present invention.

Preferably, electroplating or electrodeposition is used to dispose a protective deposit 118 onto at least a portion of the diaphragm material deposit 116. However, sputtering and/or any other technique known in the art may be used to deposit protective deposit 118 onto at least a portion of the diaphragm material deposit 116. The protective deposit 118 is generally thinner than the diaphragm material deposit 116. However, the protective deposit 118 may be thicker than the diaphragm material deposit 116.

Figure 5:
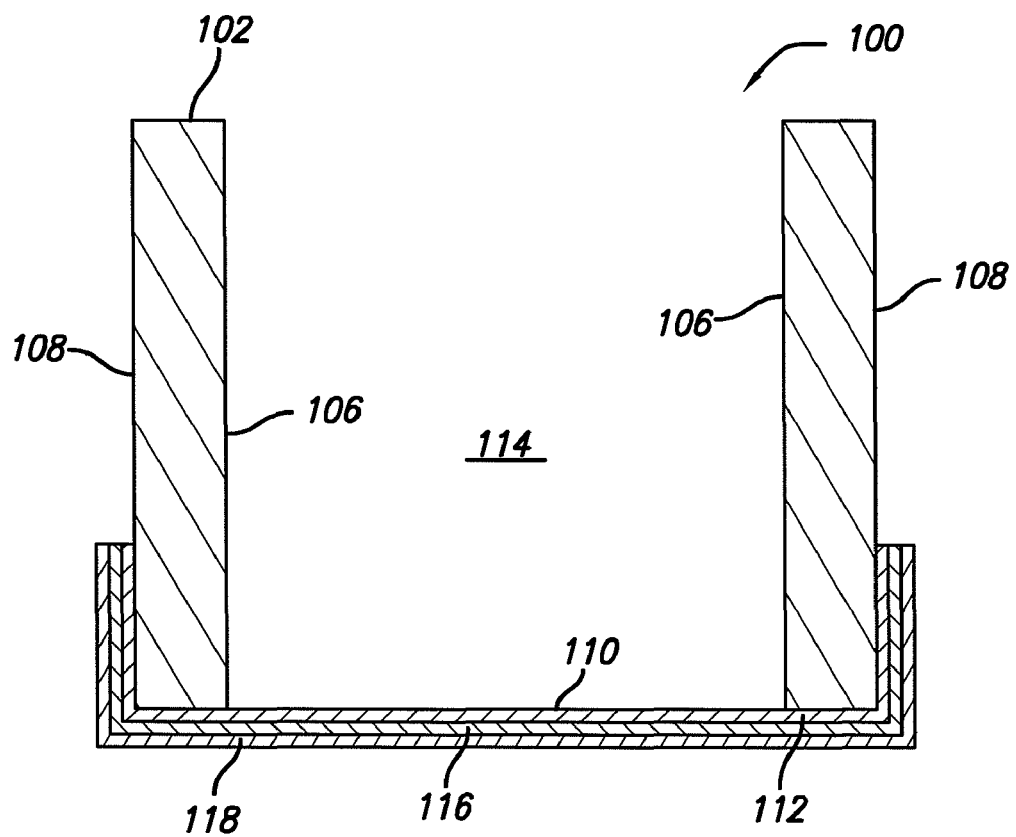
FIG. 5 is a cross-sectional view of the housing of FIG. 1 with at least a portion of the housing removed.
Figure 6:
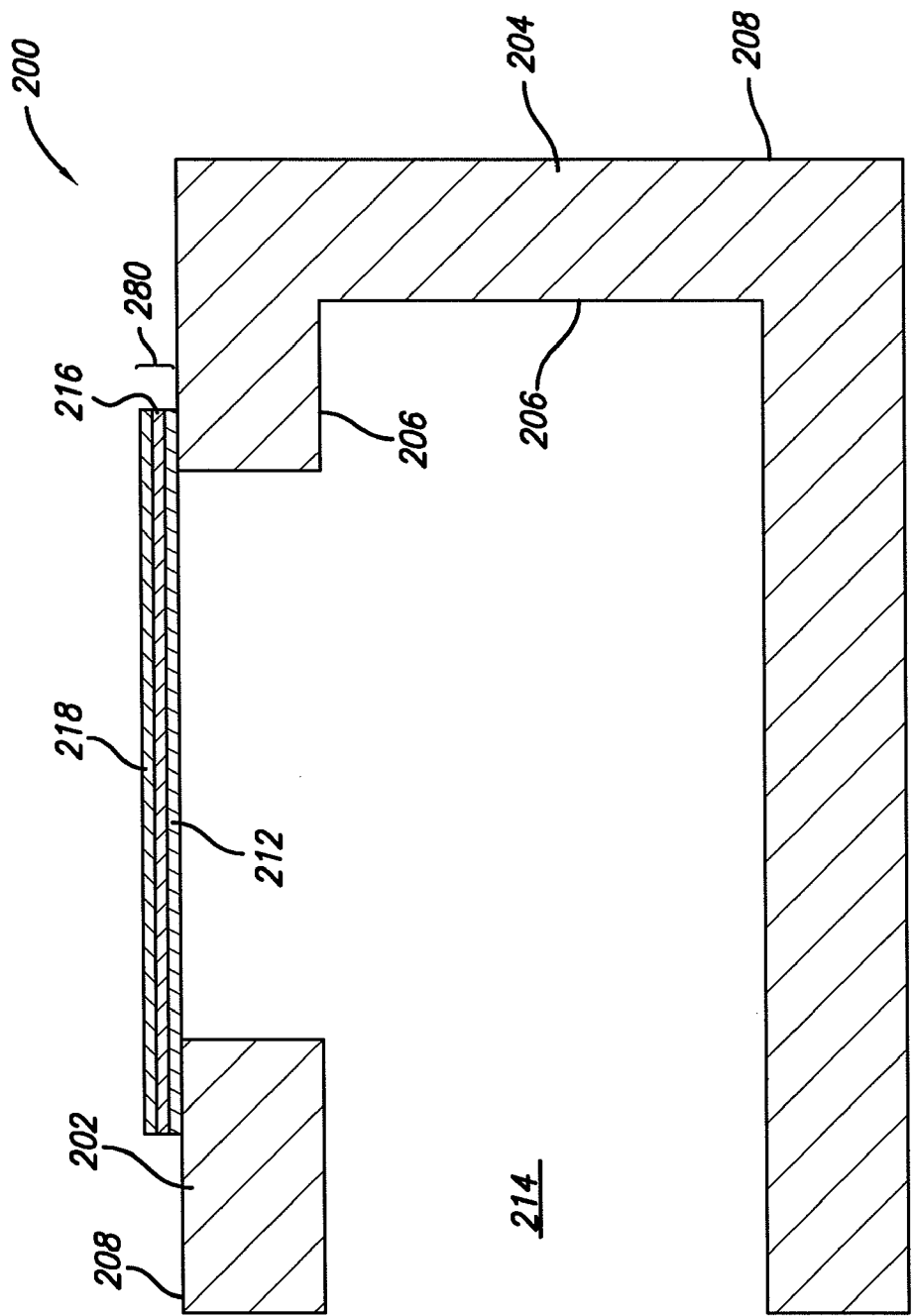
FIG. 6 is a cross-sectional view of a housing on which a diaphragm is formed on a sidewall in accordance with another preferred embodiment of the present invention.

FIG. 5 shows a preferred embodiment of a housing 100 where at least a portion of the housing 100 has been etched thereby exposing the etch stop deposit 112 to the inside or interior 114. As shown in FIG. 5, after removal or etching of a portion of the housing 100, the housing now includes a diaphragm structure comprised of etch stop deposit 112, diaphragm material deposit 116, and protective deposit 118. However, as discussed above, diaphragm structure the protective deposit 118 may be omitted.

In a preferred embodiment, at least a portion of the end 104 (not shown in FIG. 5 but shown in FIG. 4) has been chemically etched partially or completely. For example, as shown in FIG. 5, the entire end has been removed. Referring to FIGS. 4 and 5, partial or complete removal of the end 104 exposes the diaphragm structure 180 to the inside 114 of the housing 100. As shown in FIG. 5, the etch stop deposit 112 is comprised a material that is not removed through etching. Generally, at least a part of the sidewall 102 as shown in FIG. 4 also is partially removed. However, end 104 and/or sidewall 102 may be removed by any means known in the art such as wet etching methods; dry etching, such as sputtering or dissolving using reactive ions or a vapor phase etchant; or thermal methods. Any methods that etch the inner surface 106 of the end 104 and/or the sidewall 102, rather than the etch stop deposit 112, may be used to partially or completely remove the end 104 and/or the sidewall 102.

Generally, the sidewall 102 is thinner after etching than prior to etching, since a portion of the housing has been removed in FIG. 5 to expose the etch stop deposit. As such, the interior 114 of the housing 100 may define a greater volume after etching than prior to etching.

FIG. 6 shows a housing 200 in which a diaphragm is formed on a sidewall in accordance with another preferred embodiment of the invention. Preferably, the housing 200 includes at least one sidewall 202, at least one end 204, and a diaphragm structure 280. The sidewall 202 includes inner surface 206 and outer surface 208. The housing 200 defines an inside or an interior 214. Preferably, the diaphragm structure 280 includes first etch stop layer 212, diaphragm material deposit 216, and protective deposit 218. However, protective deposit 218 may be omitted.

At least a portion of the sidewall 202 has been removed in the housing 200 of FIG. 6, thereby exposing the etch stop deposit 212 to the interior 214. At least a portion of the end 204 may also be removed. Partial or complete removal of the sidewall 202 exposes the diaphragm structure 280 to the inside 214 of the housing 200. Preferably, the sidewall 202 is removed by etching, preferably chemical etching. Other methods of etching that may be used include other wet etching methods or dry etching, such as sputtering or dissolving using reactive ions or a vapor phase etchant. Any material that preferably etches the inner surface 206 of the sidewall 202 rather than the etch stop deposit 212 may be used.

Figure 7:
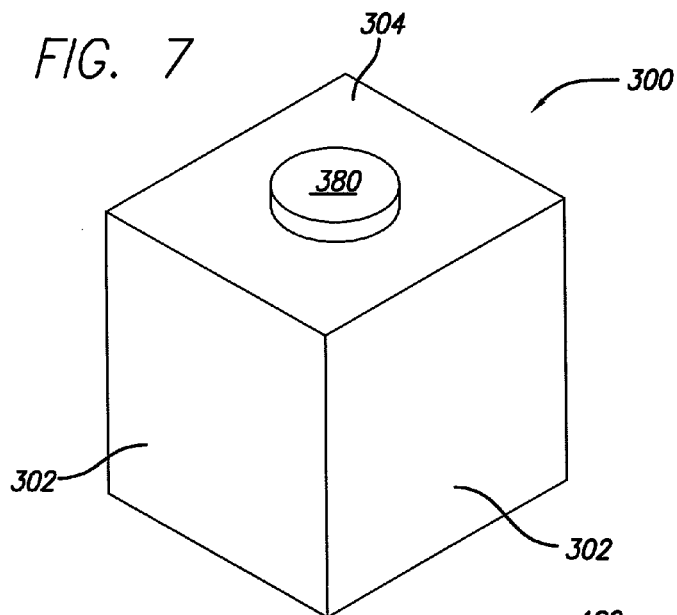
FIG. 7 is a perspective view of a housing that is rectangular in shape on which a diaphragm has been formed on an end in accordance with another preferred embodiment of the invention.

FIG. 7 shows a perspective view showing a housing 300 on which a diaphragm structure 380 has been formed on an end 304. The housing 300 is rectangular in shape and includes four sidewalls 302 and at least one end 304. The diaphragm structure 380 was formed using the methods described above.

Figure 8:
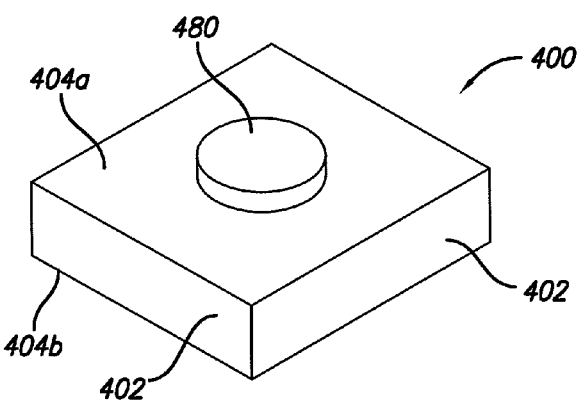
FIG. 8 is a perspective view of a plate on which a diaphragm has been formed in accordance with another preferred embodiment of the present invention.

FIG. 8 shows a perspective view of a plate or a flat plate capsule 400 on which a diaphragm structure 480 has been formed. The plate 400 preferably includes four sides 402 and top and bottom 404a and 404b (not shown). The top 404a includes diaphragm structure 480. Preferably, the diaphragm structure 480 includes diaphragm material deposit and may include an etch stop deposit layer and/or a protective deposit layer. The plate 400 is preferably comprised of metal or the like.

In a preferred embodiment, the diaphragm structure 480 is formed on the plate 400 as follows: the plate 400 is machined flat and clean. The cleaned side 404a is electroplated with a material such as nickel or nickel cobalt to a thickness suitable for the pressure range of the finished diaphragm structure 480. The back side 404b is masked exposing an area large enough for the diaphragm to be formed. The assembly is then etched with a material that preferentially etches the plate 400 and not the electroplated layer; thereby exposing the diaphragm structure 480.

Figure 9:
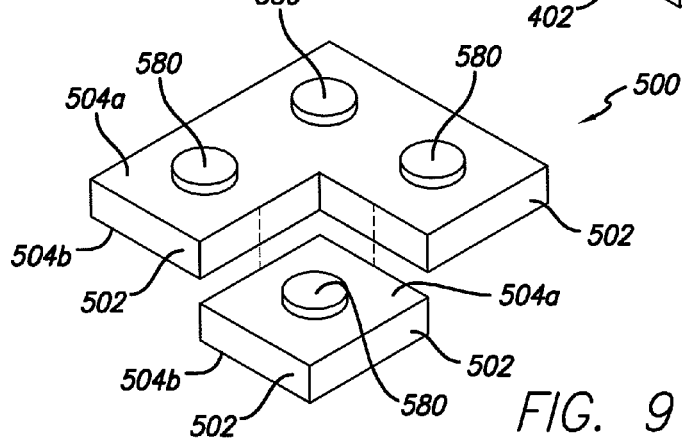
FIG. 9 is a perspective view of a plate on which a plurality of diaphragms have been formed in accordance with another preferred embodiment of the invention.

FIG. 9 shows a perspective view of a plate or a flat plate capsule 500 on which a plurality of diaphragm structures 580 has been formed. The plate 500 preferably includes four sides 502 and top and bottom 504a and 504b. The top 504a includes the plurality of diaphragm structures 580.

In a preferred embodiment, the plurality of diaphragm structures 580 are formed using the methods as described in FIG. 8. The diaphragm structures 580 may be formed in large groups, as shown in FIG. 9. This may be particularly useful in manufacturing and/or scale-up operations. Once formed, the diaphragm structures 580 may be singulated. As shown in FIG. 9, one diaphragm structure (not labeled) is singulated, or cut apart, preferably using a laser or a diamond saw. However, other means of cutting may be used. In addition, any number of diaphragm structures 580 may be formed on the plate 500. For example, a plate of 4×4 of diaphragm structures (for a total of 16) may be formed using the methods described herein.

Figure 10:
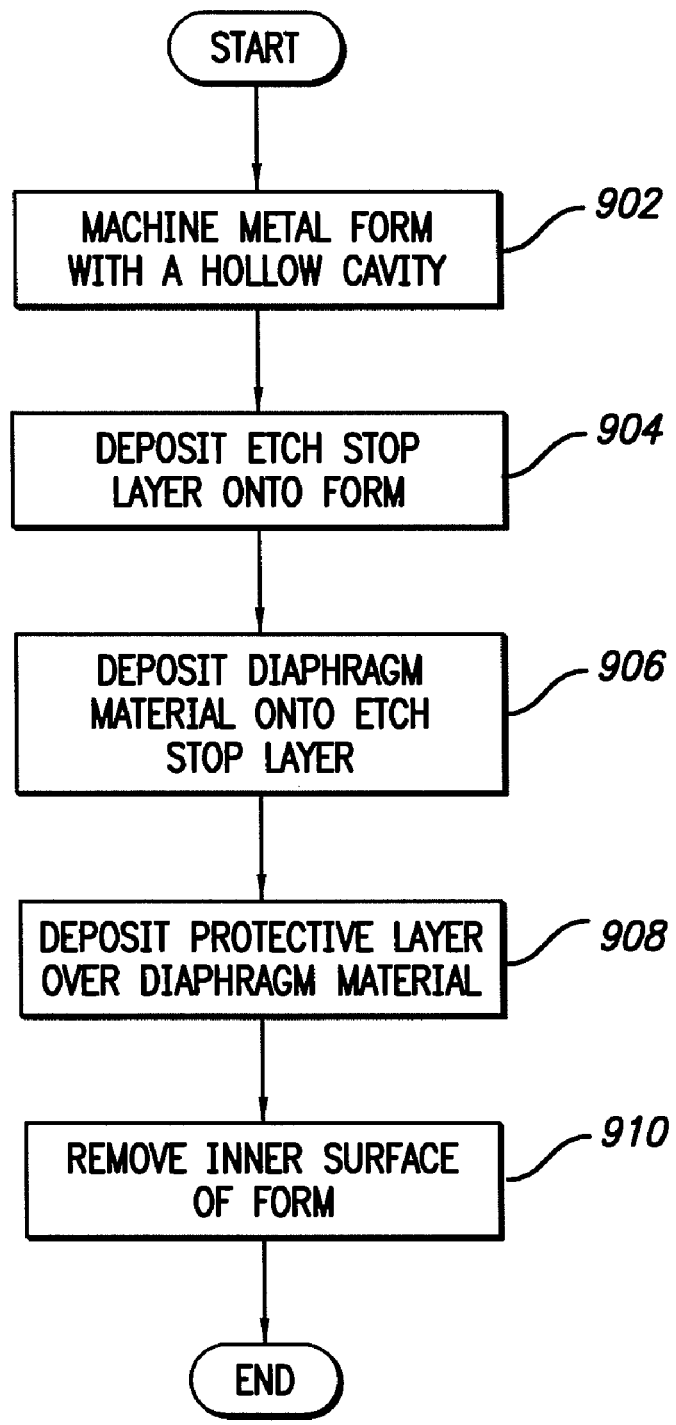
FIG. 10 is a flow diagram of a method of forming a diagram on a housing in accordance with a preferred embodiment of the present invention.

FIG. 10 illustrates a process 900 for producing diaphragms and membranes in accordance with the preferred embodiments of the invention described above. For example, process 900 begins with step 902, where a metal form is machined with a hollow cavity or an interior, thereby forming a conduit. The machined metal form may produce a tube that is round or rectangular. In step 904, an etch stop deposit layer is deposited on the outside of the form. A diaphragm material is deposited over the etch stop layer in step 906. A protective layer is deposited over the diaphragm material deposit in step 908, and at least a portion of the inner surface of the form is removed, preferably by etching, in step 910. Generally, the etching is continued until the desired internal dimension is reached through etch concentration and time control and until at least a portion of the etch stop layer is exposed.

However, in step 904, the etch stop deposit layer may be deposited on the inside of the form. As such, in step 910, at least a portion of the outer surface of the form may be removed. In addition, the inner surface of the form may be removed before the protective layer is deposited on the diaphragm layer, without departing from the scope of the present invention.

FIG. 11 shows a preferred embodiment of a housing 600 in which a diaphragm is formed on an inner surface 606 of an end 604 of the housing 600. At least a portion of the housing 600 has been removed from the outside of the housing 600, thereby exposing the etch stop deposit 612 to the outside of the housing 600. As shown in FIG. 11, at least a portion of the end 604 (depicted with dotted lines) has been removed, preferably by etching an outside of the housing 600. After the removal or etching step at least a portion of the end 604, the housing 600 now includes a diaphragm structure comprising etch stop deposit 612, a diaphragm material deposit 616, and a protective deposit 618. It is to be understood that the diaphragm structure is formed according to the methods described above.

FIG. 12 shows a preferred embodiment of the housing 700 in which a diaphragm is formed from a sidewall in accordance with another preferred embodiment of the invention. Preferably, the housing 700 includes at least one sidewall 702, at least one end 704, and a diaphragm structure 780. The sidewall 702 includes inner surface 706 and outer surface 708. The housing 700 defines an interior 714. Preferably, the diaphragm structure 780 includes etch stop layer 712, diaphragm material deposit 716, and protective deposit 718.

As shown in FIG. 12, the diaphragm is formed on the inner surface 706 of the sidewall 702. At least a portion of the sidewall 702 has been removed, thereby exposing the etch stop deposit 712 to the outside of the housing 700. At least a portion of the end 704 may also be removed. Partial or complete removal of the sidewall 702 exposes the diaphragm structure 780 to the outside of the housing 700. It is to be understood that the diaphragm structure 780 is formed according to the methods described above.

In a preferred embodiment, the housing as depicted in FIG. 11 or FIG. 12 may include additional structures machined on the exterior, such as a tapered wall to a diaphragm, a hole leading to the diaphragm, a circumferential diaphragm, or any other design/structure requiring machining on the exterior surface. This may be particularly useful in applications wherein a smooth contiguous interior surface is preferred.

In a preferred embodiment, the present invention allows for the formation of the diaphragm in a low to zero stress environment. This is further enhanced by the use of nickel cobalt zero stress electroforming. Formation of the diaphragm in this type of environment reduces and preferably eliminates long term drift and/or leaking and cracking. Preferably, the diaphragm formation process of the present invention does not require heating. The diaphragm formation with a contiguous structure is formed to eliminate stress concentration (as opposed to a copper plug, which has a discontinuous seam).

In a preferred embodiment, the methods of the present invention allow for the formation of the diaphragm without the need for density control. Density control may be used, however, to reduce forming or machining costs.

In a preferred embodiment, the methods of the present invention do not require selective masking. However, selective masking may still be used to protect features made by machining or earlier forming steps.

In another preferred embodiment, the diaphragm structures themselves may be used in some applications. They may be formed separate from the housings/plates of the invention, or cut out of the housings/plates of the invention to be used in other devices.

The embodiments described above are exemplary embodiments of the present invention. Those skilled in the art may now make numerous uses of, and departures from, the above-described embodiments without departing from the inventive concepts disclosed herein. Accordingly, the present invention is to be defined solely by the scope of the following claims.

What is claimed is:

1. A housing comprising:
   at least one sidewall, wherein the sidewall comprises inner and outer surfaces, the inner surface defining a portion of a boundary of an inside of the housing,
   an etch stop deposit disposed over at least a portion of the housing, and
   a diaphragm material deposit disposed over at least a portion of the etch stop deposit,
   wherein the at least a portion of the housing defines an etching such that at least part of the etch stop deposit is exposed to one of an outside of the housing or the inside of the housing through the etching.

2. The housing of claim 1, further comprising a protective deposit disposed over at least a portion of the diaphragm material deposit.

3. The housing of claim 1, wherein the part of the at least a portion of the housing has been removed, thereby exposing the etch stop deposit to the inside.

4. The housing of claim 3, wherein at least a portion of the sidewall has been removed.

5. The housing of claim 3, further comprising at least one end, wherein at least a portion of the end has been removed.

6. The housing of claim 1, wherein the part of the at least a portion of the housing has been removed, thereby exposing the etch stop deposit to an exterior of the housing.

7. The housing of claim 6, wherein at least a portion of the sidewall has been removed.

8. The housing of claim 6, further comprising at least one end, wherein at least a portion of the end has been removed.

9. The housing of claim 1, wherein the housing has a substantially round cross-section.

10. The housing of claim 1, wherein the housing is an implantable medical device.

11. A structure comprising:
    front and back surfaces,
    a plurality of etch stop deposits disposed over at least a portion of the front surface, and
    a plurality of diaphragm material deposits each disposed over at least a portion of one of the etch stop deposits,
    wherein the structure defines etchings from the back surface to the front surface of the structure such that at least a part of each of the plurality of etch stop deposits is exposed from the back surface through the etchings.

12. A method of isolating a diaphragm on a housing, the method comprising:
    depositing an etch stop deposit on at least a portion of the housing,
    depositing a diaphragm material deposit on at least a portion of the etch stop deposit, and
    removing at least a part of the at least the portion of the housing over which the etch stop deposit is deposited to expose the etch stop deposit to either an inside or an outside of the housing.

13. The method of claim 12, further comprising etching at least a portion of an inner surface of the housing, thereby exposing at least a portion of the etch stop deposit to the inside of the housing.

14. The method of claim 12, further comprising etching at least a portion of an outer surface of the housing, thereby exposing at least a portion of the etch stop deposit to the exterior of the housing.

15. The method of claim 12, wherein depositing the etch stop deposit comprises electroplating the etch stop deposit onto the housing.

16. The method of claim 12, wherein depositing the diaphragm material deposit comprises electroplating the diaphragm material deposit on at least a portion of the etch stop deposit.

17. The method of claim 12, further comprising depositing a protective deposit on at least a portion of the diaphragm material deposit.

18. The method of claim 12, wherein the housing is a sensor.

19. A plate comprising:
    front and back surfaces,
    an etch stop deposit disposed on at least a portion of the front surface, and
    a diaphragm material deposit disposed over at least a portion of the etch stop deposit,
    wherein the plate defines an etching from the back surface to the front surface of the plate such that at least part of the etch stop deposit is exposed from the back surface through the etching.

20. The plate of claim 19, further comprising a mask disposed over at least a portion of the back surface.

21. A method of forming a plurality of plates, the method comprising:
    providing the structure of claim 11; and
    cutting the structure to provide a plurality of plates.

22. The housing of claim 1, wherein the etch stop deposit is selected from the group consisting of gold, platinum, or rhodium.

* * * * *